(12) United States Patent
Teucher et al.

(10) Patent No.: US 12,400,748 B2
(45) Date of Patent: Aug. 26, 2025

(54) MEDICAL DEVICE WITH DOSE HELPER FUNCTIONALITY INCLUDING TIME ZONE OR LOCATION DETERMINATION

(71) Applicant: Sanofi-Aventis Deutschland GmbH, Frankfurt am Main (DE)

(72) Inventors: Axel Teucher, Frankfurt am Main (DE); Frank Roethke, Frankfurt am Main (DE); Florian Schauderna, Frankfurt am Main (DE); Marcus-Meinolf Dittrich, Frankfurt am Main (DE); Andrew Tubb, Surrey (GB); Timothy Golnik, Bridgewater, NJ (US); Joseph Flaherty, Salem, NH (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 17/520,502

(22) Filed: Nov. 5, 2021

(65) Prior Publication Data

US 2022/0059206 A1 Feb. 24, 2022

Related U.S. Application Data

(62) Division of application No. 14/418,204, filed as application No. PCT/EP2013/066754 on Aug. 9, 2013, now Pat. No. 11,587,662.

(30) Foreign Application Priority Data

Aug. 10, 2012 (EP) .................................... 12180168

(51) Int. Cl.
*G16H 20/17* (2018.01)
*A61M 5/172* (2006.01)
(Continued)

(52) U.S. Cl.
CPC ............. *G16H 20/17* (2018.01); *G06F 16/22* (2019.01); *G16H 20/10* (2018.01); *G16H 40/63* (2018.01);
(Continued)

(58) Field of Classification Search
None
See application file for complete search history.

(56) References Cited

U.S. PATENT DOCUMENTS

| 6,039,251 A | 3/2000 | Holowko et al. |
| 2002/0147135 A1 | 10/2002 | Schnell |

(Continued)

FOREIGN PATENT DOCUMENTS

| CN | 1994484 A | 7/2007 |
| CN | 102300501 A | 12/2011 |

(Continued)

OTHER PUBLICATIONS

Toussi M, Choleau C, Reach G, CahanéM, Bar-Hen A, Venot A. A novel method for measuring patients' adherence to insulin dosing guidelines: introducing indicators of adherence. BMC Med Inform Decis Mak. Dec. 5, 2008; 8 :55; 9 pages (Year: 2008).*

(Continued)

*Primary Examiner* — Rachel L. Porter
(74) *Attorney, Agent, or Firm* — McCarter & English, LLP

(57) ABSTRACT

A medical device for supporting health control is provided. An example medical device can include a receiver unit configured to receive information regarding a current location of the medical device or a current time-zone of the medical device, a user interface, a storage unit storing instructions, and one or more processors configured to execute the instructions to cause the medical device to perform operations. Examples of operations include deter- (Continued)

mining a current location of the medical device and/or a current time zone of the medical device from the received information, providing a dose helper functionality employing a titration method to determine and/or recommend a basal long-acting insulin dose value or a corrective amount of basal long-acting insulin to be administered by a patient to the patient based on a measured physiological parameter, information about hyperglycemic events, the determined current location and/or current time zone of the medical device.

21 Claims, 7 Drawing Sheets

(51) Int. Cl.
   *G06F 16/22* (2019.01)
   *G16H 20/10* (2018.01)
   *G16H 40/63* (2018.01)
   *H04L 67/12* (2022.01)
(52) U.S. Cl.
   CPC ... *A61M 5/1723* (2013.01); *A61M 2205/3334* (2013.01); *A61M 2230/201* (2013.01); *H04L 67/12* (2013.01)

(56) References Cited

U.S. PATENT DOCUMENTS

| | | | |
|---|---|---|---|
| 2004/0133390 A1* | 7/2004 | Osorio | A61B 5/4094 702/178 |
| 2004/0143346 A1 | 7/2004 | Francis et al. | |
| 2005/0192846 A1* | 9/2005 | De Zwart | A61N 1/3625 705/3 |
| 2006/0009734 A1 | 1/2006 | Martin | |
| 2006/0075001 A1* | 4/2006 | Canning | G06F 8/65 707/999.203 |
| 2007/0142822 A1 | 6/2007 | Remde | |
| 2009/0069745 A1 | 3/2009 | Estes et al. | |
| 2010/0057044 A1* | 3/2010 | Hayter | A61M 5/142 604/504 |
| 2010/0204557 A1 | 8/2010 | Kiaie et al. | |
| 2010/0256047 A1* | 10/2010 | Sieh | A61P 3/10 702/19 |
| 2010/0292634 A1 | 11/2010 | Kircher, Jr. et al. | |
| 2011/0124996 A1* | 5/2011 | Reinke | A61M 5/14248 600/300 |
| 2011/0184342 A1 | 7/2011 | Pesach et al. | |
| 2011/0193705 A1* | 8/2011 | Sekura | A61J 7/04 340/573.1 |
| 2012/0053843 A1* | 3/2012 | Tubb | G01N 33/49 702/19 |
| 2012/0109100 A1 | 5/2012 | Estes et al. | |
| 2012/0116196 A1 | 5/2012 | Tubb | |

FOREIGN PATENT DOCUMENTS

| | | |
|---|---|---|
| CN | 102356625 A | 2/2012 |
| CN | 102369029 A | 3/2012 |
| CN | 102405011 A | 4/2012 |
| CN | 102448513 A | 5/2012 |
| CN | 102481101 A | 5/2012 |
| EP | 1232762 A1 | 8/2002 |
| EP | 1281351 A2 | 2/2003 |
| EP | 1948112 A1 | 7/2008 |
| JP | 2004-532055 A | 10/2004 |
| JP | 2006-126930 A | 5/2006 |
| JP | 2009-532768 A | 9/2009 |
| JP | 2012-516735 A | 7/2012 |
| WO | 2003/049695 A2 | 6/2003 |
| WO | 2006/016339 A1 | 2/2006 |
| WO | 2007/041843 A1 | 4/2007 |
| WO | 2007/112034 A2 | 10/2007 |
| WO | 2010/062898 A1 | 6/2010 |
| WO | 2010/089304 A1 | 8/2010 |
| WO | 2010/089307 A1 | 8/2010 |
| WO | 2010/091102 A1 | 8/2010 |
| WO | 2010/114257 A2 | 10/2010 |
| WO | 2010/117841 A1 | 10/2010 |
| WO | 2011/008520 A2 | 1/2011 |
| WO | 2012/122520 A1 | 9/2012 |

OTHER PUBLICATIONS

Goldberg et al., Management of type 2 diabetes. N Engl J Med. Jan. 17, 2008;358(3):293-7.

European Office Action for Application No. 22150463.2, dated Apr. 20, 2022, 11 pages.

International Preliminary Report on Patentability for Application No. PCT/EP2013/066754, dated Feb. 19, 2015, 14 pages.

International Search Report and Written Opinion for Application No. PCT/EP2013/066754, dated Dec. 3, 2014, 18 pages.

Japanese Office Action for Application No. 2015-525903, dated May 9, 2017, 4 pages.

Russian Office Action for Application No. 2015107825/14, dated Aug. 14, 2017, 11 pages.

Taiwanese Office Action for Application No. 10620347350, dated Apr. 5, 2017, 10 pages.

Taiwanese Office Action for Application No. 10621280980, dated Dec. 19, 2017, 15 pages.

U.S. Appl. No. 14/418,204, filed Jan. 29, 2015, 2015-0161339, U.S. Pat. No. 11,587,662, Feb. 21, 2023, Issued.

Chandran et al., Have Insulin, Will Fly: Diabetes Management During Air Travel and Time Zone Adjustment Strategies. Clin Diabetes. 2003;21(2):82-85.

European Office Action for Application No. 22150463.2, dated Dec. 20, 2024, 8 pages.

\* cited by examiner

MEDICAL DEVICE WITH DOSE HELPER FUNCTIONALITY INCLUDING TIME ZONE OR LOCATION DETERMINATION

CROSS REFERENCE TO RELATED APPLICATIONS

The present application is a divisional of U.S. patent application Ser. No. 14/418, 204, filed Jan. 29, 2015, which is a U.S. National Phase Application pursuant to 35 U.S.C. § 371 of International Application No. PCT/EP2013/066754 filed Aug. 9, 2013, which claims priority to European Patent Application No. 12180168.2 filed Aug. 10, 2012. The entire disclosure contents of these applications are herewith incorporated by reference into the present application.

TECHNICAL FIELD

The present invention relates to a medical device for supporting health control, in particular for providing information for glycemic control, a respective medical system, a method for providing such information, a respective computer program and a respective computer program product.

BACKGROUND

People with diabetes are either deficient in insulin or are unable to make sufficientinsulin to overcome underlying insulin resistance or to normalize the glucose metabolism. In order to achieve a better glycemic control or even to regain almost full glycemic control often basal insulin or insulin glargine treatment is used which is based upon a set of rules set for periodic blood glucose measurements in order to obtain information on the progress of the treatment. With regard to this it has to be considered that the blood glucose levels fluctuate throughout the day. A "perfect glucose level" would mean that glucose levels are always in a range of 70 to 130 mg/dl or 3.9 to 7.2 mmol/l and undistinguishable from a person without diabetes.

In order to achieve this or to get as close as possible to such a "perfect glycemic control", blood glucose values are monitored once or several times during the day, as relying on their own perception of symptoms of hyperglycemia or hypoglycemia is usually unsatisfactory as mild to moderate hyperglycemia causes no obvious symptoms in nearly all patients. If the blood glucose value is too high, e.g. over 130 mg/dl, insulin or insulin analogues can be administered.

For the insulin therapy long-acting basal insulin or insulin glargine, which are long-acting basal insulin analogues, are used. These insulin or insulin analogues are usually given once daily to help control the blood sugar level of patients with diabetes. The advantage of long-acting basal insulin or insulin glargine is that they have a duration of action of more than 24 hours or even more with a less peaked profile than NPH insulins. Thus, the profile more closely resembles the basal insulin secretion of the normal pancreatic β-cells.

For good or perfect glycemic control the dose of basal insulin or insulin glargine has to be adjusted for each individual in accordance with a blood glucose level to be achieved. Usually, the dose of insulin or insulin glargine is increased from an initial dose to a final dose over a certain time period until the specific blood glucose value, typically the fasting blood glucose (FBG) value has reached the target range. In practice, such titration can be done by the health care professionals (HCPs). However, the patient may be empowered and trained by the HCPs to do their own titration. Such a self-titration can be supported by an intervention from a third party support or service or some intermediate combination.

In everyday use, basal insulin or insulin glargine is typically under-dosed. Thus, there remains a gap between the initial dosing and an optimal dosing for achieving perfect or almost perfect glycemic control. This has a number of negative effects which better titration could help to eliminate. For example, if patients are not titrated, their blood sugar does not come down and as a result they do not feel better in the short term. Moreover, in the long term their HbA1c remains high and their health suffers. Thus, the patients may feel that their treatment is not working, and they may lose interest in the therapy or discontinue treatment.

Due to the almost peakless profile, basal insulin and insulin glargine are simple totitrate. Meanwhile, there is an array of approaches that physicians use for titration. Generally, these approaches suggest a specific dose adjustment within a specific time period until the target FBG is achieved. Each of these algorithms comes with specific rules, e.g. that the dose should not be increased if the blood glucose value (BG value) was below 70 mg/dl (low blood sugar) in the last week. Furthermore, HCPs may set a FBG different from the initial target to suit the patient.

Document EP 1 281 351 A2 describes a diabetes management system which enables glycemic control for a subject. The described system includes an insulin delivery unit, aglucose sensor and a control unit. The control unit includes a processor unit that receives glucose value readings from the glucose sensor, executes an algorithm that predicts a glucose value at a predetermined time in the future, compares the predicted glucose value with the predetermined glucose value range, and determines a corrective amount of insulin to be administered when the predicted glucose value lies outside of the predetermined glucose value range. The glucose unit also includes a communication unit that transmits the corrective amount to the delivery unit.

In the document WO 2010/089304 A1 a medical device for providing information for glycemic control is described. The device comprises storage means arranged to store data, receiving means arranged to receive blood glucose value data and security data, data processing means arranged to execute a first processing function for modifying data retrieved from the storage means and to execute a second processing function for providing information for glycemic control based on the blood glucose value data and data retrieved from the storage means, validating means arranged to validate the received security data and to provide validation data corresponding to the validation of the received security data, and safety means arranged to control an execution of at least a predetermined function out of the first and second processing functions based on the validation data. The first processing function is a processing function for adjusting the profile parameters for a selected dose adjustment profile. The second processing function is a processing function for stepwise adapting a dose of insulin based at least on the selected dose adjustment profile and thereby determining the value for the dose of insulin to be set.

Considering the above medical devices, in particular the above mentioned processing functions, the problem arises that it is necessary to provide a safe access to a dose helper functionality which determines and recommends an insulin dose value or a dose value of another medicament to be administered by the patient in order to reduce the possibility of harm which might be caused by a wrong dose suggestion to the patient.

SUMMARY

The above problem is solved by a medical device with the features of claim 1.

In particular, the device comprises:

first storage means arranged to store an initial data matrix with at least one initial parameter set containing at least two initial data entries for one parameter of a dose helper functionality;

receiving means arranged to receive initialization data and/or security data, preferably from a second storage means, for example provided by a hardware key;

selecting means operable to select based at least in part on the initialization data one data entry for each initial parameter set as initial data or one initial parameter template containing a reference to one data entry for each initial parameter set as initial data;

and first activation means arranged to activate, preferably based at least in part on the security data, execution of the dose helper functionality based on the selected initial data.

The above solution provides a safe access to the dose helper functionality. The safe access in particular comprises that the dose guidance function of the dose helper functionality needs to be initiated and activated before use. If the dose guidance function is not activated, the dose helper part of the device will not function, although other unprotected functions will work, for example the blood glucose measurement.

The present invention successfully realizes an easy method for activation of the dose helper functionality in combination with the patient-specific selection of initial data for the algorithm behind the dose helper functionality. Therein, for a parameter of the dose helper functionality that needs initial data the data matrix stores a parameter set containing at least two initial data entries.

The dose helper functionality according to the present invention refers to a titration method which determines and/or recommends a medicament dose value or its corrective amount, preferably an insulin dose value, to be administered by the patient, based on a measured physiological parameter, preferably based on measured blood glucose values, more preferably based on measured FBG values, and/or information about hypoglycemic and/or hyperglycemic events and/or other data which starts at a starting dose and guides the patient step by step to a final dose of basal long-acting insulin that keeps the patient in a pre-defined target glucose level. Preferably, the dose helper functionality is realized as a computer program unit fully separate, for example, from a unit that determines a blood glucose value. The dose helper functionality may be terminated by the user and/or the HCP and/or the program itself, for example if the program detects missing compliance of the patient. After termination the dose helper functionality may be reinitialized and reactivated again by the described initialization and activation procedure.

For activation of the dose helper functionality initialization data are transmitted to the medical device containing information about which initial data shall be used in the titration method. In particular, not the whole initial data for each parameter itself are transmitted but initializing information that—in a manner of speaking—point to the corresponding initial parameter template or the corresponding data entry of each initial parameter set. For example, the initial parameter sets may be arranged in one or more lists, where each list entry is numbered. Then, only the number of the list entry may be transmitted to address and select a desired data entry. Each data entry of an initial parameter set may suit to another patient group or titration algorithm. In a preferred embodiment the initial data matrix containing all initial data is permanently stored within the medical device and cannot be manipulated. This inventive device and respective method ensures in an easy and cost effective way that the titration method works after activation with correct, well adjusted initial data for each parameter. If, for example, the titration process and the body's reaction is better understood, a change of initial data for certain patient groups can be realized in an easy way without change of the medical device. Only the transmitted initialization data of, for example, a hardware key, may be changed.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound.

wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein m a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin;Lys(B3), Glu(B29) human insulin; Lys(B28), Pro(B29) human insulin; Asp(B28) human insulin;human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-litho-cholyl-Y-glutamyl)-des(B30) human insulin; B29-N-(m-carboxyheptadecanoyl)-des(B30) human insulin and B29-N-(m-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE00IO),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipres sin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain(VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammomum ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The initialization and activation shall be provided by an authorized HPC, preferably using a physical hardware key or a remote computer containing the initialization data and/or security data in the second storage means. This hardware key may be separate from the device and may be connected physically to the device via a connector, e.g. an electrical connector like USB (universal serial bus). Transferring initialization data and/or security data wirelessly may also be an option, for example using near field communication or Bluetooth™.

In another embodiment, the hardware key may be realized as a memory card, for example in the format of a SIM-card, a mini-SIM, a nano-SIM or an embedded SIM. Such a card may be removed from a card body or card holder prior use.

Preferably, the hardware key is a passive device without its own energy supply, such as a battery. The hardware key is a not-programmable device so that there is no bi-directional communication with the device. The hardware key may comprise a read only memory(ROM) containing the preferably encrypted initialization and/or security data. The hardware key is only used to select respective initial data out of the initial data matrix, stored in first storage means of the medical device. Therefore the initialization data preferably contains the information about the location of the data entry (or the locations of the data entries) in the initial data matrix for each parameter set, wherein each parameter set refers to a different parameter of the algorithm. The initialization data may also contain an index or identification means, e.g. a number, of the template for the initial data matrix comprising a reference to one respective initial data entry for each initial parameter set. The hardware key may be plugged into respective electrical receptacle of the medical device.

Preferably, the HCP is provided with at least two, more preferred with at least three, different hardware keys, wherein each key comprises specific initialization data and/or specific security data for a different patient group. Each hardware key may be reusable. In another embodiment, the hardware key may be provided for single use.

In another embodiment, the initialization data and/or security data may be provided by a remote computer connected to the medical device by wire or wireless. Alternatively, the initialization and/or security data may be provided by the user, e.g. an HCP, through a computer system. The initialization and/or security data may be entered on a computing device via a user interface using keys, a keypad, a touchpad or a microphone (for voice control). Alternatively, the user may receive the initialization data and/or security data via an internet page provided e.g. by the manufacturer of the medical device or its selling partner. The user may then select a certain parameter template through the user interface of the computing device.

In a preferred embodiment, the medical device comprises second activation means arranged to activate and/or control execution of initialization of the dose helper functionality based at least in part on the initialization data and/or the security data. For example, insertion of the hardware key into the connector of the device may be detected automatically. Then, data messages are exchanged between the medical device and the hardware key that identify the connected device as an activation key. After identification, the initialization and/or security data may be read out of the hardware key, that means for example the index information or information on the location of the initial data and/or security data.

In an alternative example without a hardware key, a remote computer may provide a security code which has to be entered into the device using a user interface. The security code may be provided by the remote computer only in the case where a correct question code provided by the device in advance was entered into the computer, for example into a query field of a (local) software application or of an internet application, or to a phone helpline.

The medical device further provides data processing means which are arranged to execute a first processing function for modifying at least one of the selected initial data entries. In particular, this is the case if one or more of the initial data entries are provided as default initial data, for example the starting dose of the dose helper functionality. During the initialization procedure the HCP or other user is asked whether he/she likes to change this default value, e.g. the default initial dose value. The user may confirm the default value or change it using a user interface.

In a further embodiment the device provides safety means arranged to control an execution of the first processing function based at least in part on the security data. The security data, for example a password, may be provided by the hardware key or the remote computer. For example, the initialization procedure asks for a password before the user is able to change default initial values.

The initialization and/or activation of the dose helper functionality may be accessed via a respective settings operation mode (menu) of the device.

The medical device further comprises blood glucose measurement means arranged for determining a blood glucose value and to provide blood glucose value data corresponding to the measured blood glucose value. Alternatively to a blood glucose measurement means, the receiving means may be arranged to receive the blood glucose value from the blood glucose measuring means.

In order to run the dose helper functionality the blood glucose measurement means may in particular contain the functionality to tag a glucose measurement result as a fasting blood glucose value (FBG value), i.e. a blood glucose value under fasting condition. The device may propose tagging a glucose measurement result as a fasting blood glucose value, when the measurement is made at a certain time of the day, for example in the morning hours between 6:00 and 9:00 o'clock. The user then may confirm that the measurement is a fasting blood glucose value, e.g. by pressing a key on the user interface. The user may adjust the time window during which a fasting glucose measurement tag is suggested during initialization or later, e.g. to a time window between 5:30 and 8:00 o'clock.

The device may also assign other tags to certain glucose measurements. For example, the device may assign a "before lunch" or "after lunch" tag, or a "before dinner" or "after dinner" tag to a certain glucose measurement. Again, the device may suggest a certain tag based on the time of the day, e.g. during a given time window.

The device may therefore keep track of the time, e.g. by implementing an electronic timer, or a first clock and calendar function. To enable tagging of a glucose measurement as a fasting glucose measurement, the device may have to determine, whether the last blood glucose measurement that was related to a meal, such as the "after dinner" glucose measurement, dates back at least, for example, eight hours. In order to determine this time difference correctly without influence of time change because of travelling, the device may have to account for time shifts that may occur for example when travelling to a different time zone. For this purpose, the device may comprise a separate second clock which is separate from the clock showing the actual time to the user. In order to determine a time difference reliably, the second clock may not be adjustable by the user. The second clock may derive its energy from a separate battery (for example a coin cell) which is separate from the battery or other energy source of the device and in particular separate from the energy source of the first clock.

In a further embodiment the second activation means are arranged to activate and/or control execution of initialization of a dose helper function further dependent on an expiration date or validity data provided by the hardware key. Therefore each hardware key comprises an expiration date or validity data in its second storage means like ROM. This expiration date, for example referring to a date which is two or three years after the production date, or the validity data referring to a time period is read and compared to the actual date of the device. In case that the expiration date is exceeded or the validity data not met, the initialization and/or activation of the dose helper function may be prevented. In this case it is assumed that the initialization and/or security data of the hardware key are too old, outdated or a high probability exists that these data are tampered. In the medical device, means are provided to prevent the user from manipulating the system date in order to override the expiration date or validity data. The expiration date or the validity data may be written to the second storage means during production as the initialization data and/or the security data. Additionally, the expiration date may be printed or written on the outer surface of the hardware key so that the user, e.g. the HCP easily recognizes whether the key is outdated.

In another embodiment each hardware key retains a serial number in its storage means for traceability reasons. Preferably the serial number is also read out by the medical device during initialization of the dose helper functionality.

The receiving means of the medical device further comprises a user interface, a USB interface, a mini-USB interface, an IEEE 1394 interface, an ISO/IEC 7810:2003 interface, an ETSI TS 102 221 interface, an interface according to JEDEC Design Guide 4.8, SON-8 and/or a wireless interface adapted to receive the initialization data and/or the security data. The initialization data contains at least the information about which initial data entry is to be selected by the selecting means of the device from the initial data matrix for each parameter set, namely separate for each parameter set, or as a reference to a template containing the information for more than one or all parameter sets. Alternatively or additionally, via one of the above-mentioned interfaces a universal code for multi-use as well as a single-use code may be transmitted as security data. Those codes may be handed out or directly typed in on the user interface by the authorized HCP. It is also possible that the initialization means generate a code/question during activation from which a remote computer calculates a response which then has to be entered via the user interface as confirmation. The remote computer could be contacted e.g. via telephone or internet. Also smartphones solutions (for example an app with internet access) may be possible. Another possibility would be to use a time-based system like secure ID.

Further, the ownership of the software may be used as authorization. The software may create a response as code as described above. Another option would be the direct connection between the device and a computer via cable for activation. Then the software needs to be secured by the security data.

The above problem is further solved by a medical system with the features of claim 8.

In particular the system comprises a medical device as it is described above and a hardware key or other device comprising second storage means arranged to store initialization data and/or security data and transmitting means arranged to transmit the initialization data and/or the security data stored in the second storage means to the receiving means of the medical device.

In particular by using a separate hardware key it is easy for the HCP to initialize or activate the dose helper functionality as described above.

As it is explained above, the second storage means, may comprise an expiration date or validity data in an embodiment of the present invention.

It is preferred if the system comprises a set of at least two hardware keys, preferably of at least three hardware keys, wherein each hardware key of the set comprises different initialization data and/or also different security data. This set of hardware keys allows the HCP to better adapt the dose helper functionality of the device to different patients with different disease patterns.

With the same advantages as the device above, the method with the features of claim 11 solves the problem mentioned above.

In particular the method comprises the steps of:
  receiving initialization data and/or security data preferably from a second storage means, for example provided by a hardware key;
  selecting based at least in part on the initialization data one data entry of each initial parameter set of an initial data matrix as initial data or one initial parameter template containing a reference to one data entry for each initial parameter set of the initial data matrix as initial data; and
  activating, preferably based at least in part on the security data, execution of the dose helper functionality based on the selected initial data.

Preferably, the method comprises the further step of activating and/or controlling of execution of initialization of the dose helper functionality based at least in part on the initialization data or the security data.

For the same reasons it is advantageous to run a computer program for providing information for glycemic control at a processor, wherein the computer program comprises:
  code for receiving initialization data and/or security data preferably from a second storage means, for example provided by a hardware key;
  preferably code for activating and/or controlling of execution of initialization of the dose helper functionality based at least in part on the initialization data or the security data;
  code for selecting based at least in part on the initialization data one data entry of each initial parameter set of an initial data matrix as initial data or one initial parameter template containing a reference to one data entry for each initial parameter set of the initial data matrix as initial data; and
  code for activating, preferably based at least in part on the security data, execution of the dose helper functionality based at least in part on the selected initial data.

Further, a computer program product, comprising a computer-readable medium bearing a computer program code embodied therein, for use with a computer, wherein the computer program code comprises the computer program as described above.

In another embodiment, in particular in the case in which the dose helper functionality (titration method) is realized as an app within a smartphone, an internet connection, a GSM connection, a GPS receiver or other means for determining the actual location and/or the time-zone of the device may be provided. Hence, the device comprises for example a GSM receiver, a GPS receiver or module, a radio broadcast receiver capable of interpreting an RDS signal and/or a radio clock receiver like DCF 77 in order to determine the local time. Further, in case that the method is realized as an app within a smartphone a built-in GPS module may determine its location using public hotspots. The dose helper functionality of the device may provide a warning display and/or may not calculate a dose suggestion or dose increase in case that these means for determining the location of the device assess that the location of the device has changed to a time zone, where the time change is more than a predefined maximum time change value, for example more than three hours. A patient facing a time change larger than the predefined maximum time change is assumed to have difficulties meeting the requirements of dose administration intervals for long-acting insulin and fasting time for determining correct FBG values and the patient may be locked out from the dose helper functionality.

In case that the patient faces the situation that he/she is locked out from using the dose helper functionality, in particular in an app, for several reasons, for example if the device may not have been activated and the glucose readings logbook does not have a sufficient number of glucose readings to carry out an adequate calculation, or if the patients has travelled over time zones with a time change more than a predefined maximum time change, the patient may become frustrated or afraid because he or she may not know how to handle this situation. In order to encourage the patient to be confident, i.e. seek the advice of his/her predefined HCP (the contact information of the at least one predefined HCP are saved in the memory of the device), the app may pull the HCP's phone number or another contact information and may offer the patient to get into contact with HCP by just pressing at least one button that is displayed on the same screen. The direct contact may be established by a phone call or by sending a message, e.g. a text message, or e-mail to the HCP, for example requesting the HCP to get in touch with the patient.

The HCP's contact information may be programmed into the app by the time the dose helper functionality is initialized by the HCP. For example, during initialization procedure the HCP may be asked for his/her telephone number or other contact information. Alternatively, the HCP's contact information is required to be entered on the app's first start-up just after activation.

The above-mentioned advantages as well as other advantages of various aspects of the present invention will become apparent to those of ordinary skill in the art by reading the following detailed description with the explanation of the accompanying drawings. All features described above and below and/or illustrated per se or in any combination form the subject-matter of the invention, independent of their inclusion in the claims or their back-reference.

BRIEF DESCRIPTION OF THE FIGURES

Exemplary embodiments of the present invention are described herein with reference to schematic drawings, in which.

DETAILED DESCRIPTION

The following paragraphs will describe various embodiments of the invention. For exemplary purpose only, most of the embodiments are outlined in relation to a medical device or system providing glycemic control and the respective method. However, the used terminology and the description of the embodiments with respect to the medical device and system are not intended to limit the principles and ideas of the invention to such a single device or system.

Also, the detailed explanations given in the background of the invention section above are merely intended to better understand the constraints of an insulin treatment or a treatment with other hormones. Furthermore, the titration methods described herein can be applied to basal, premixed and mealtime insulin. In the following, the term insulin is used for all kinds of insulin, including long-acting insulin, and insulin glargine unless otherwise stated.

Figure 1:
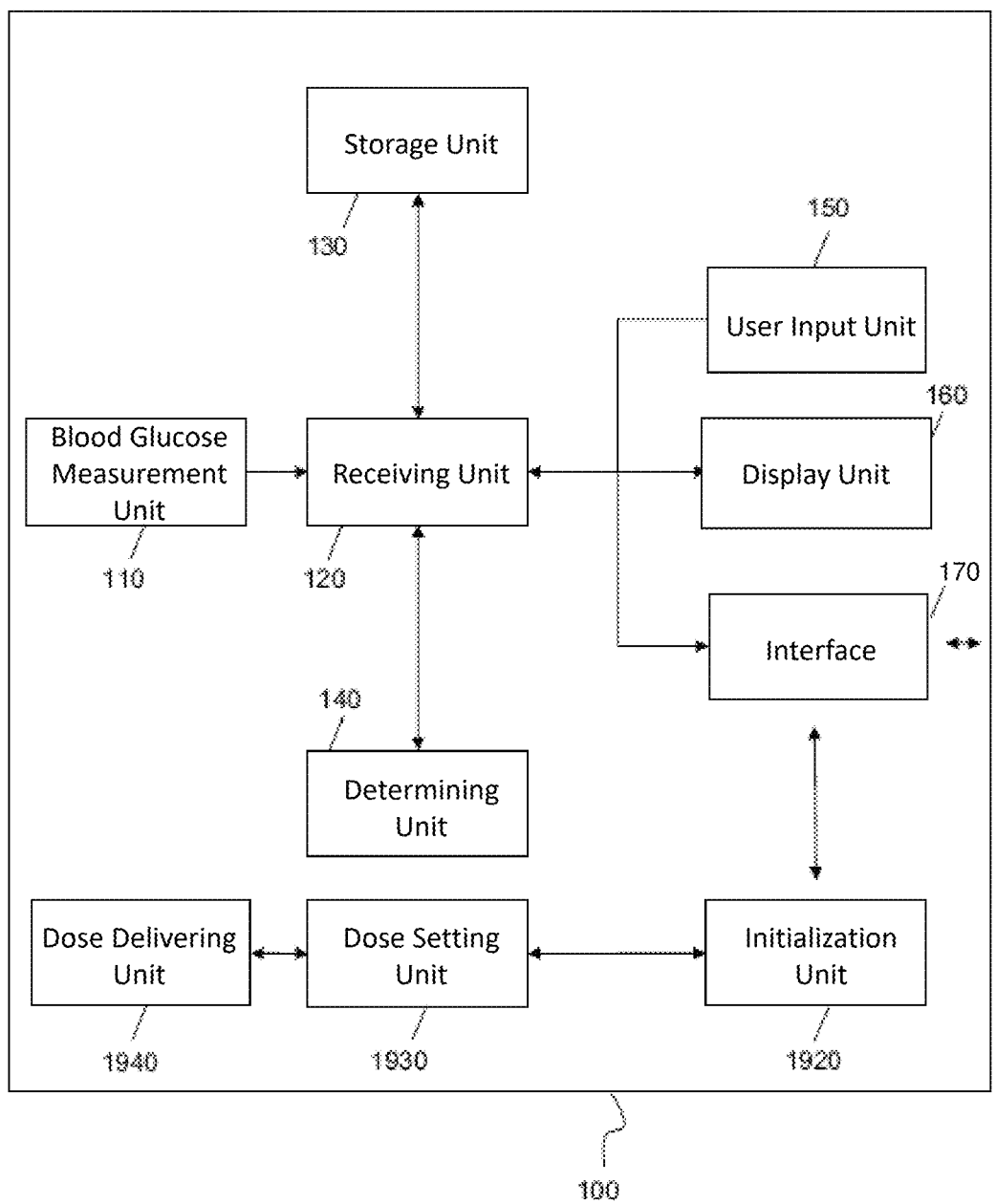
FIG. 1 is a diagram of the medical device according to a preferred embodiment of the invention.

FIG. 1 is a schematic diagram of the medical device according to a preferred embodiment of the invention. Preferably, the medical device 100 comprises a blood glucose measurement unit 110, which is arranged to measure the blood glucose level e.g. of the user of the medical device for example by means of a measurement strip in a well-known way. In this case the measurement unit 110 comprises an interface and a slot for the test strip with e.g. leads. The blood glucose measurement unit 110 is connected to a receiving unit 120, which is arranged to forward e.g. blood glucose value data received from blood glucose measurement unit 110 to the storage unit 130. Alternatively, the receiving unit 120 may retrieve stored data such as e.g. blood glucose value data from the storage unit 130 and forward it to a determining unit 140. Alternatively, the receiving unit 120 directly forwards the blood glucose value data received from the blood glucose measurement unit 110 to the determining unit 140.

Receiving unit 120 is further connected to user input unit 150 (user interface). The user input unit 150 is arranged to receive input from the user of the medical device 100 for example by keys. The user input data are forwarded from the user input unit 150 to the receiving unit 120, which either forwards it to the determining unit 140 or to the storage unit 130.

Furthermore, the medical device 100 preferably comprises a display unit 160, which is connected to the receiving unit 120 as well. Preferably, the display unit 160 receives data to be displayed from the receiving unit 120. Preferably, the medical device 100 additionally comprises a further interface 170, for example a wired interface such as a serial port, a USB interface, a mini-USB interface, or a wireless interface such as an IRDA interface, Bluetooth™ interface, etc., in order to receive data and/or to transmit data. The interface 170 is preferably connected to the receiving unit 120 in order to receive data from the receiving unit 120 and to forward data to the receiving unit 120.

As outlined above, the medical device 100 preferably comprises a blood glucose measurement unit 110. Preferably, the blood glucose measurement unit 110 is arranged to measure the blood glucose level in the blood of e.g. the user by testing a drop of blood on the above mentioned test strip. The measured blood glucose value is then transformed to blood glucose value data and forwarded preferably immediately or on demand to the receiving unit 120. Alternatively, the blood glucose measurement unit 110 is arranged to measure the blood glucose level of e.g. the user via infrared diagnosis or an alternative contactless measurement method.

According to a further alternative the blood glucose measurement unit 110 is implanted in the body of the user of the medical device 100 and forwards the data to the receiving unit 120 either via a wired connection or via a wireless connection. Preferably, such an implanted blood glucose measurement unit 110 is a continuous measurement sensor e.g. based on a bio chip which allows a continuous closed loop control. In the latter case the blood glucose measurement unit 110 preferably forwards the blood glucose measurement value data to the receiving unit 120 via interface 170. According to a further alternative the medical device 100 does not comprise a blood glucose measurement unit 110 which measures the blood glucose values, but receives blood glucose value data from an external unit.

The measurement of the blood glucose measurement is preferably triggered by the receiving unit 120 which sends a respective signal to the blood glucose measurement unit 110. According to one preferred alternative the receiving unit 120 receives a trigger signal generated based on user input which is received via user input unit 150. Alternatively, the trigger signal is generated automatically by a timer unit or by determining unit 140.

Preferably, the receiving unit 120 is represented e.g. by the input ports and output ports of a microprocessor or a bus system managing the data handling between several functional units. This includes bus systems, such as e.g. Advanced Microprocessor Bus Architecture bus systems implemented in a microprocessor or external bus systems connected to a microprocessor. Via the receiving unit 120, data are retrieved from the storage unit 130 on demand and forwarded to the determining unit 140, to the display unit 160 or to the interface 170. Moreover, the receiving unit 120 forwards control signals, such as trigger signals or control signals e.g. to the blood glucose measurement unit 110, the display unit 160 or the interface 170.

The storage unit 130 (storage means) is arranged to store data entered via the user input unit 150, data received by the blood glucose measurement unit 110, data processed by the determining unit 140 and/or data received via interface 170. Furthermore, storage unit 130 is arranged to provide the stored data to the determining unit 140, to the display unit 160 and/or to the interface 170. The storage unit 130 is preferably implemented as a semiconductor memory. Alternatively, it is implemented as a hard disk memory or an on-chip memory of the determining unit 140.

According to the invention the storage unit 130 comprises an initial data matrix with at least one initial parameter set containing at least two initial data entries for one parameter of the dose helper functionality. Such parameters may be the initial dose or the maximum dose, so that in this case the initial data matrix contains two initial parameter sets, one for the initial dose and one for the maximum dose, each comprising at least two initial data entries. Further examples of such parameters are given below.

The determining unit 140 is preferably a microprocessor or any other functional unit capable of processing data.

The user input unit 150 is preferably implemented as one or more push buttons or alternatively as so called soft keys wherein the function of the respective soft key is displayed on the display unit 160. Alternatively, the user input unit 150 is a key board or a touch screen. Alternatively, the user input unit 150 comprises a microphone for receiving speech input so that data can be entered via speech input.

The display unit 160 preferably comprises an LCD or LED display. Preferably, the display can display a number of alphanumerical characters so that e.g. the actual measured blood glucose value can be displayed together with additional instructions for the user. Alternatively, the display unit 160 comprises a graphic display in order to display graphs or graphics such as icons. Further the display of the display unit 160 may comprise a touchscreen.

The interface 170 is preferably a wireless interface, such as IRDA, Bluetooth™, GSM, UMTS, ZigBee, or WI-FI, etc. Alternatively, the interface is a wired interface, such as a USB port, mini-USB port, serial port, parallel port, network card, etc., for receiving and transmitting data. In a further alternative the medical device 100 does not comprise an interface 170.

According to another alternative medical device 100 comprises in addition to the interface 170 a memory card reader or a memory card reader interface. The memory card reader is preferably adapted to read information from a memory card, such as a Flash memory card, or any type of SIM card. For this, the memory card comprises a memory, wherein preferably a selected algorithm together with corresponding parameters and a history of the blood glucose values and doses administered, etc. is stored. Thus, in the case that the medical device 100 has a defect, the relevant data may still be stored on the memory card which can be easily removed from the memory card reader of the medical device 100 and transferred to a new medical device 100. Moreover, the memory card 100 may be used in order to provide information on the history of the treatment to e.g. an HCP. In an example embodiment, the memory card is the above described hardware key. Then, the memory card comprises preferably only ROM.

In the case that the memory card is a SIM card providing subscriber identification for a mobile communication network and the interface unit 170 is additionally a mobile communication interface, the basic functions of the medical device 100 can be unlocked by the provider of the SIM card via a telecommunication channel. This additionally offers the possibility that the medical device 100 can communicate with other telecommunication devices via predefined channels, such as UMTS or GSM. Via the international mobile subscriber identity, also called IMSI, stored in the SIM card, the medical device 100 identifies itself within the network and, thus, can be addressed via the network. In such a case the medical device 100 can be easily checked, remote controlled, updated, monitored, etc., via interface unit 170, e.g. by addressing the mobile communication unit with a phone number.

Furthermore, the medical device 100 is able to transmit data via SMS, e-mail or via mobile internet connection. Moreover, this offers the possibility to locate the medical device 100 in an emergency case.

Furthermore, the medical device 100 comprises an initialization unit 1920 capable to communicate with the interface unit 170. The initialization unit 1920 is connected to a dose setting unit 1930 for proposing a dose to be administered according to the signals received from the interface unit 170 and the determining unit 140. The dose setting unit may be further connected to a dose delivering unit 1940. Preferably, the initialization unit 1920, the dose setting unit 1930 and—if applicable—the dose delivering unit 1940 form a functional and structural unit comprising the dose helper functionality which is separated from the other components shown in FIG. 1. The dose helper functionality may be initialized and activated and deactivated as described above without influencing the operation of the blood glucose measurement.

In an embodiment of the present invention, the dose setting unit 1930 and the dose delivering unit 1940 may form an insulin pen or insulin pump or an inhalator device which receives signals from a transceiver unit in order to deliver a dose determined by the dose setting unit 1930. According to a preferred alternative the dose delivering unit 1940 forwards a signal to the transceiver unit that the dose set has been successfully delivered. In an alternative embodiment the device 100 does not contain a dose delivering unit 1940 and the dose setting unit 1930 may display the determined insulin dose value at the display of the display unit 160. In this case the patient administers the suggested dose or another dose by himself/herself using, for example with an insulin pen. The patient preferably has the possibility to enter the administered dose into the device using e.g. the user interface.

In the case that the blood glucose measurement unit 110 is a continuous sensor which is e.g. implanted and the dose delivering unit 1940 is an insulin pump an automatic delivery system is provided. In the case that this full automatic delivery system asks for a user confirmation, for example in case of a proposed dose increase, a semi closed loop control is provided.

In another embodiment the above mentioned units of the medical device or parts of these units may be divided and provided within at least two separate devices comprising separate housings which are connectable to each other. In a further embodiment one or more of these units or parts of these units may be realized as an app on a smart phone or a mobile computer, for example a tablet computer or a laptop computer.

Figure 2:
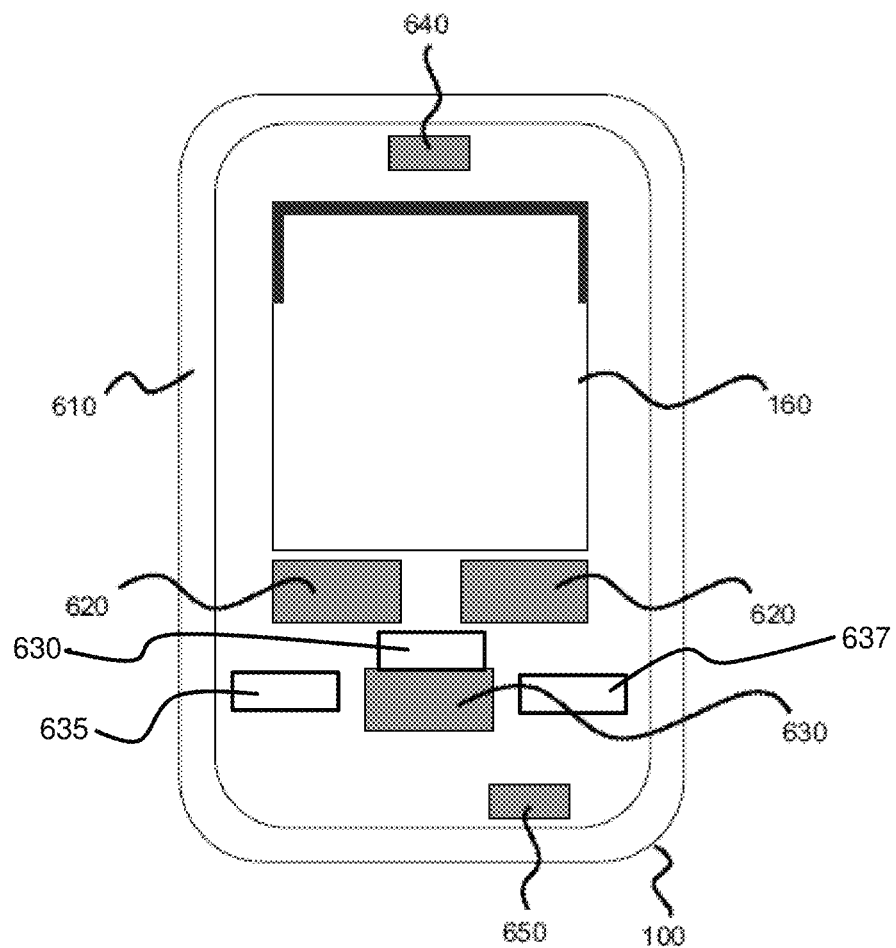
FIG. 2 is another diagram of the medical device shown in FIG. 1.

FIG. 2 shows a further schematic diagram of the medical device 100 according to a preferred embodiment of the invention. In particular, FIG. 2 shows details of the housing and the display of the medical device 100 according to a preferred embodiment of the invention. The medical device 100 comprises housing 610 wherein in the upper side of the housing 610 the display unit 160 is placed. Next to the display unit 160, the housing 610 shows a lower section wherein soft keys 620, navigation keys 630 and a back key 635 are placed. The soft keys 620 are placed directly next to the display, preferably to the lower left and lower right side of the display. Thus, the display can show the function actually assigned to the soft keys 620. Additionally, a dose helper key 637 is provided which is preferably accommodated on the right hand side of the navigation keys 630.

Preferably, a soft key is a button located alongside the display unit 160. This soft key performs the function dependent on the text shown near it at the moment on the display.

The navigation keys 630 are used for scrolling through the menu selections displayed in the display unit 160, navigating to the next item in a list or increasing or decreasing the value of an editable field. Preferably, by pressing the upper navigation key 630, one can scroll up the menu selections or increase a value, and by pressing the lower navigation key 630, one can scroll to the lower part of the menu selections or decrease a displayed value. The back key 635, preferably arranged at the left hand side of the navigation keys is used for returning the user to the previous screen shown on display unit 160. This key may also serve as the power button if the device is off. Alternatively, a navigation pad or a touch screen is used for navigation.

By pressing the dose helper key 637, which may be highlighted by a different color compared to the other keys, the dose helper functionality of the device is started, preferably only in case that this functionality is initialized and activated by an HCP or the user.

Preferably, medical device 100 comprises a loudspeaker 640 connected to an acoustic module for output acoustic signals such as acoustic alerts or speech. Moreover, the medical device 100 preferably also comprises a microphone 650 for speech input, voice recognition or for communicating via a network connection.

Figure 3:
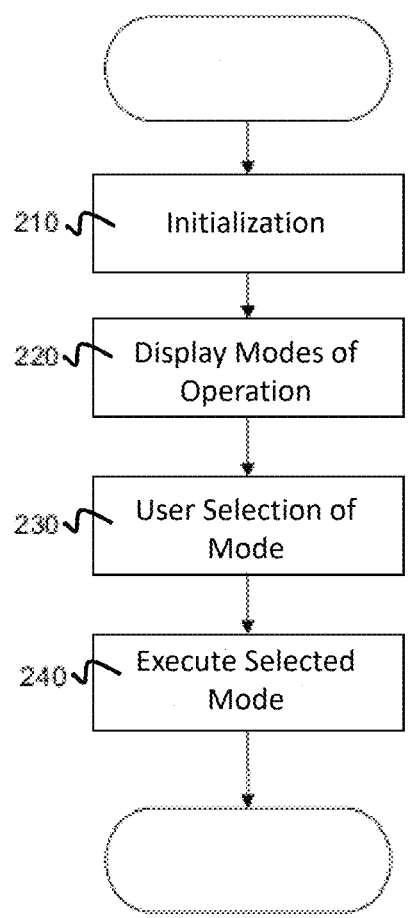
FIG. 3 is a flow diagram illustrating steps of operation of the medical device according to a preferred embodiment of the invention.

As shown in FIG. 3, the medical device 100 is preferably capable to perform a number of operating processes. According to a preferred alternative after switching on, e.g. by pressing the back key 635, the medical device 100 performs initialization step 210 for initializing the functional components of the medical device 100. After this, the different operation modes of which the medical device 100 is capable, are displayed in the display step 220. Preferably, modes such as "Measure BG", "History" and/or "Settings" can be selected in step 220. In step 230 the user selects one of the displayed operation modes via the user input unit 150. In step 240 the selected operation mode is executed.

According to an alternative version of the operation process steps 220 and 230 may be skipped in the case that a specific operation mode is preselected. In that case, after initialization 210, the preselected operation mode, which is either preselected by the user or automatically selected in accordance with a specific event, the operating process proceeds with step 240 and executes the preselected one or more operation modes.

Depending on the operation mode, the operation process may continue after the execution of the selected mode with step 220 in order to give the user of the medical device 100 the option to choose a further operation mode or the operation process ends. In the latter case the medical device 100 is preferably switched off automatically.

Figure 4:
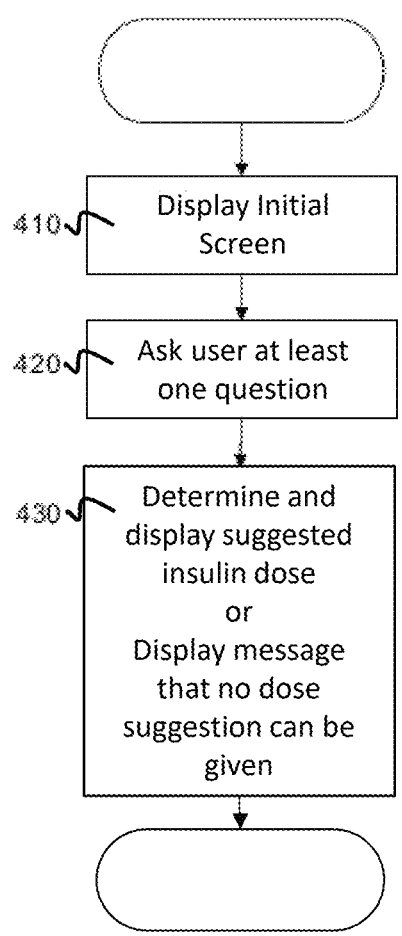
FIG. 4 is a flow diagram illustrating steps of another operating procedure of the medical device according to a preferred embodiment of the invention.

The dose helper functionality may be started by pressing the dose helper key 637 if the device is on or off. This functionality is described by means of the diagram as depicted in FIG. 4. After starting the functionality displays an initial screen in step 410 using display unit 160. After that in the next step 420 the user is asked at least one question regarding for example hypoglycemia symptoms, low blood sugar measurements (e.g. lower than 70 mg/dl) and/or taken insulin doses. Therein, the total number of questions depends on the answer to certain questions. After finishing questioning, in step 430 the device determines an insulin dose, preferably a dose of long-acting insulin, using the dose setting unit 1930 and displays the determined dose suggestion in the display of the display unit 160. Alternatively, in step 430 a message is displayed that no dose suggestion can be given to the user at this time.

The dose suggestion is determined by the dose setting unit 1930 preferably based on previous fasting FBG values and/or other measured blood glucose values, previous administered insulin doses and other lifestyle information like hypoglycemia symptoms or low blood sugar values. Additionally, exercise information, nutrition facts and additional fast-acting insulin doses as well as stress information may be considered. In particular, it is determined whether a single value of FBG or a mean value FBG is within a target blood glucose range which was previously defined for the certain user. If the single or mean FBG value is above the target range, usually a dose increase is suggested, if the single or mean FBG value is below the target range, a dose decrease may be suggested.

The screen of display unit 160 in step 430 may provide the possibility that the proposed insulin dose is confirmed and saved in case the user immediately administers the suggested dose. In this case the suggested and administered dose is saved in storage unit 130. Alternatively, the user may change the suggested dose and save it after administration.

Additionally, in step 410 it may be checked whether the current time is within a predefined time interval from the last known dose or the last dose is entered with a time less than the predefined time interval, preferably 18 hours, from the current time. In this case, the step 420 may be skipped and the display of display unit 160 may show the message that dose helper is unavailable because it is too close to the last insulin dose, or the dose helper may ask another question regarding the time of the last dose. In this embodiment it is assumed that the dose helper functionality is only used in close temporal proximity of dose administration.

In another embodiment, for dose administration a certain time or time range of day may be predefined. For example, usual dose time may be 7 p.m. and the usual dose time range between 4 p.m. and 10 p.m. In this case, another check whether the current time is between 4 p.m. and 10 p.m. may be performed during step 410. If the current time is outside this range, again, step 420 may be skipped and the display of display unit 160 may show the message that dose helper is unavailable because it can only be run at the usual dose time.

Figure 6:
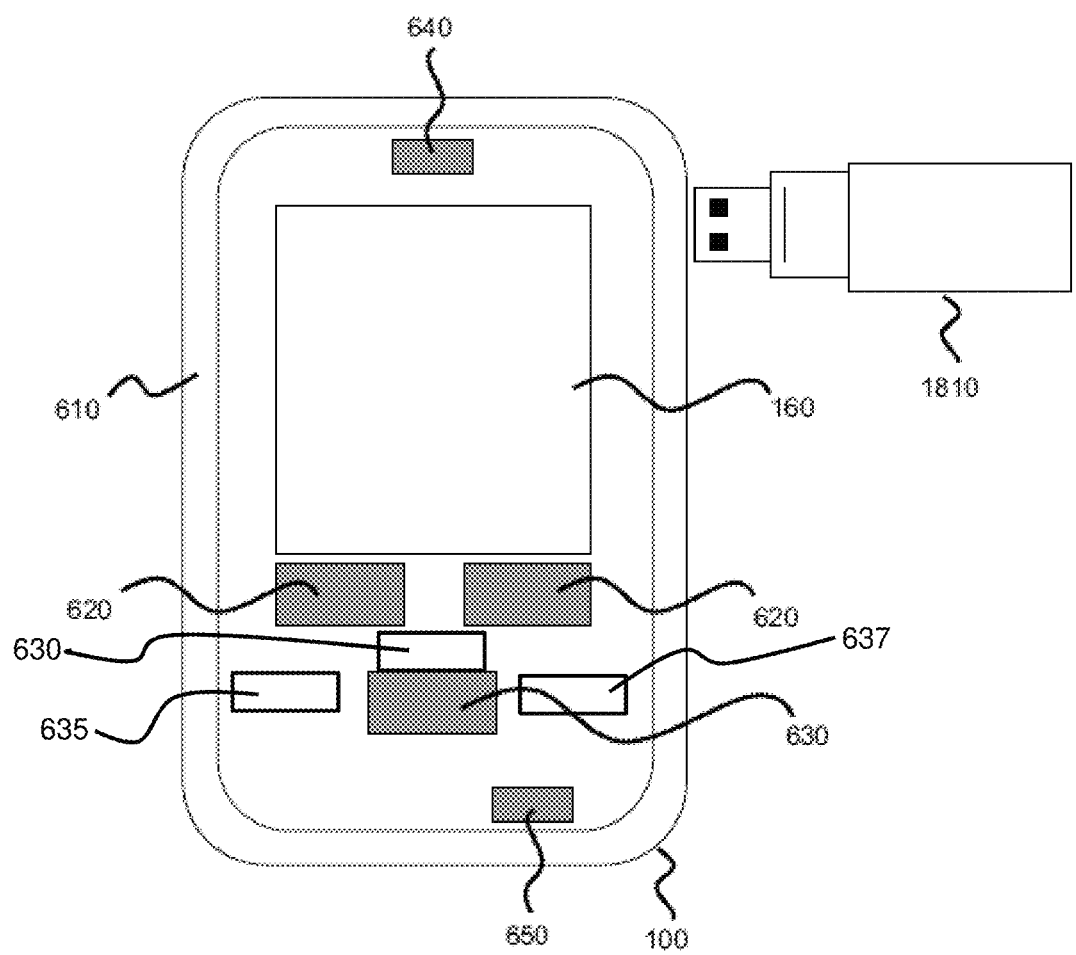
FIG. 6 is a diagram illustrating the medical system according to a preferred embodiment of the invention.
Figure 7:
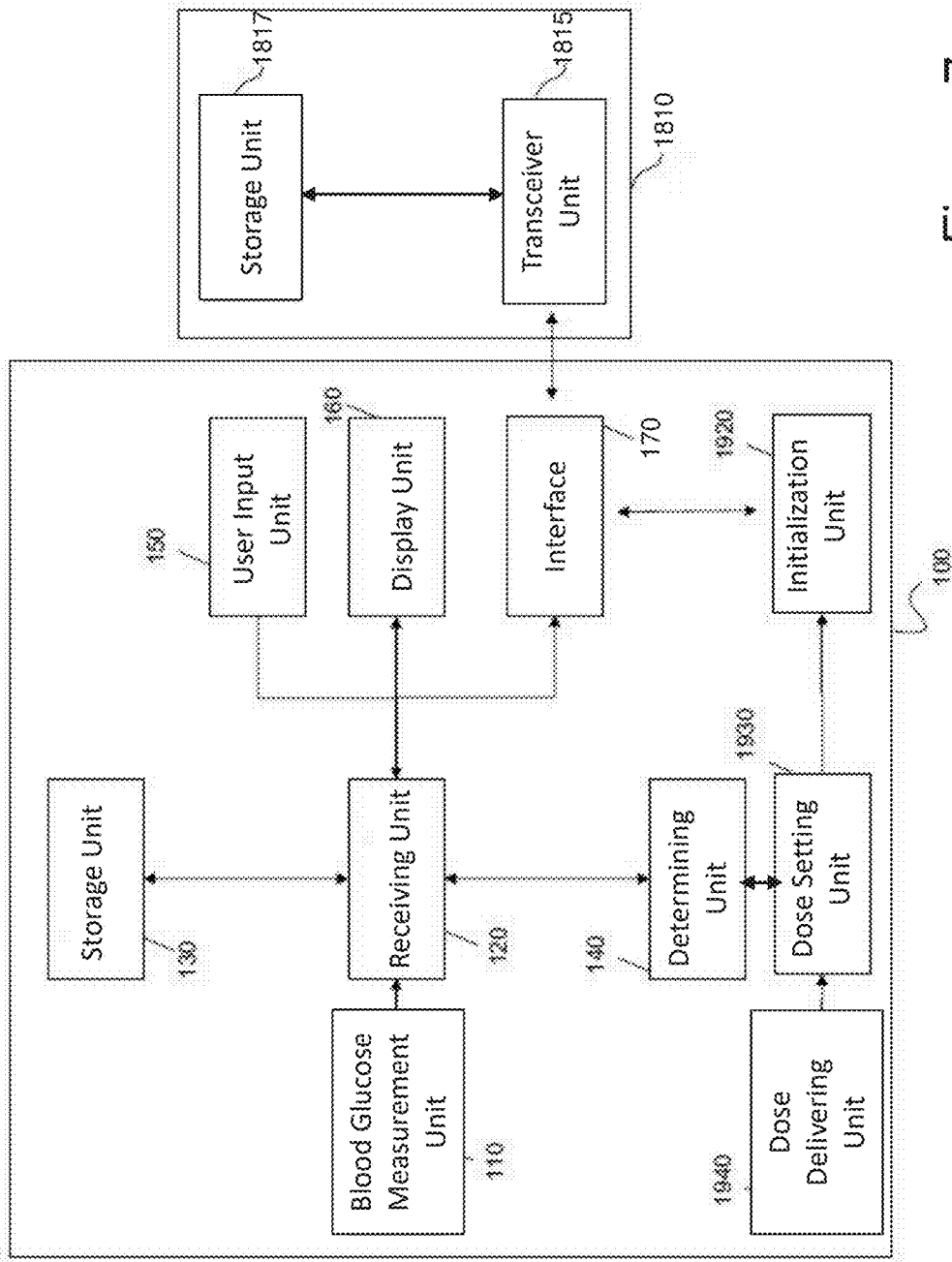
FIG. 7 is another diagram showing the medical system depicted in FIG. 6.

As described above the dose helper functionality may be initialized and activated before use or for reuse after termination, preferably by an HCP, using a hardware key as it is depicted in FIGS. 6 and 7. If the dose helper functionality is not active the device 100 may be used as a regular glucose meter. Therefore interface 170 allows the HCP to initialize the dose helper functionality of the medical device 100, for example via remote control. This will be explained in detail further below.

Further, once activated, the dose helper functionality may have an expiry date so that after passing that date the dose helper function is no longer available to the patient unless the patient consults the HCP to re-activate the dose helper functionality. Further, the patient can deactivate the dose helper functionality in the settings menu if this function is no longer needed. In addition, the dose helper functionality may be automatically de-activated if the data collected by the device indicates that using the dose helper functionality could not work as expected, for example if the blood glucose level cannot be brought in a target range.

Moreover, if the dose helper functionality is already activated using a first set of initial data entries for the parameters of the algorithm, the functionality may be modified by the HCP to use a second set of initial data entries by, for instance, connecting a different hardware key 1810 to the device in order to re-initiate or re-activate the dose helper functionality using the second set of initial data entries further on. That principle applies to other activation methods (e.g. wireless) as well.

FIG. 6 shows a schematic diagram of the medical device 100 according to a preferred alternative of the preferred embodiment of the invention. The interface 170 is e.g. a USB interface capable to receive initialization data via a hardware key 1810, for example a mini-USB stick or via a USB link. On the hardware key 1810 initialization data are stored in a ROM. In a preferred alternative, the interface 170 requests the initialization data continuously from the USB port while the initialization process is running. As long as the initialization data necessary for the initialization process can be retrieved via the USB port, the interface 170 can execute the predetermined functions. In the case that the hardware key 1810 is disconnected from the medical device 100 the interface 170 can no more receive the necessary initialization data for the initialization process. Accordingly, the display unit 160 outputs a message indicating that the initialization process was not successful.

FIG. 7 is a schematic diagram showing the medical system according to FIG. 6. Preferably, the hardware key 1810 comprises a transceiver unit 1815 which is connected to a storage unit 1817, preferably realized as a ROM. The transceiver unit 1815 is capable to communicate with the interface 170. Preferably, the transceiver unit 1815 and the interface 170 communicate via a wired data connection or via a wireless data connection.

The storage unit 1817 of the hardware key 1810 is arranged to store initialization data and/or security data, such as e.g. HCP initialization data, preferably in encrypted form, which are transmitted by the transceiver unit 1815 to the interface 170 and the initialization unit 1920. Thus, the initialization unit 1920 can configure the dose helper functionality of the medical device 100. Preferably, the initialization unit 1920 is capable to execute a predetermined first processing function as long as the hardware key 1810 is in connection with the medical device 100. In the case that the hardware key 1810 is on a remote place, such as an office of the HCP, the HCP using the hardware key 1810 can configure, modify and/or control the dose helper functionality of the medical device 100. Such a medical system offers the possibility that critical functions of the dose helper functionality of the medical device 100 are (re-)configurable via remote control only by an authorized HCP, while other functions of the medical device 100 can still be used and modified by the user of the medical device 100. Moreover, such a system may offer the possibility to directly forward alerts produced by a low FBG check or a hypoglycemic check directly to the HCP as well.

Preferably, the step of controlling the execution of the predetermined function or functions of the dose helper functionality differentiates between different authorization levels for controlling the respective predetermined functions. For example, for specific predetermined functions it is only necessary to receive the initialization and—if applicable—the security data once, for example by the HCP, so that the respective specific predetermined functions of the dose setting unit 1930 can be executed always if required, whereby other predetermined functions may be executed by the user without certain security data.

In that way it is arranged that e.g. a process for suggesting the dose to be administered (dose helper functionality) is initialized and activated by providing the initialization and—if applicable—security data before first use or after each deactivation of the dose helper functionality. After this initialization and activation the medical device 100 can be used for determining the respective dose to be administered, without any further need to receive the initialization data and/or security data again unless the functionality is not terminated or reaches the end of prescription (e.g. after half a year). Other functions, such as modifying specific data in the storage unit 130, however, require receiving the security data, for example a password each time they are executed.

Thus, it is ensured that only a specific person, such as a HCP being capable of providing the initialization data and/or security data and therefore performing the initialization and activation procedure of this functionality.

Preferably, only one hardware key 1810 is used for initialization and/or activating the dose helper functionality provided by the dose setting unit 1930. Alternatively, different initialization and/or security data are used which correspond to different authorization levels. For example, with a master security data or master key, which is preferably available for the health care professional, all predetermined first sets of functions can be initialized or/and activated. With a further security data or key, which is for a specific user, only a second set of specific predetermined functions can be initialized or/and activated.

In another preferred embodiment, for initialization and activation of the dose helper functionality each HCP is provided with a set of e.g. three hardware keys, each of which refers to a different profile for different patients. The HCP chooses one of these keys for the specific patient suitable for his/her specific disease pattern. Each key contains different initialization data and/or security data in its respective storage unit 1817. In order to differentiate the keys visually, each key may be highlighted with a different color and may show main initial data printed on its cover.

Figure 5:
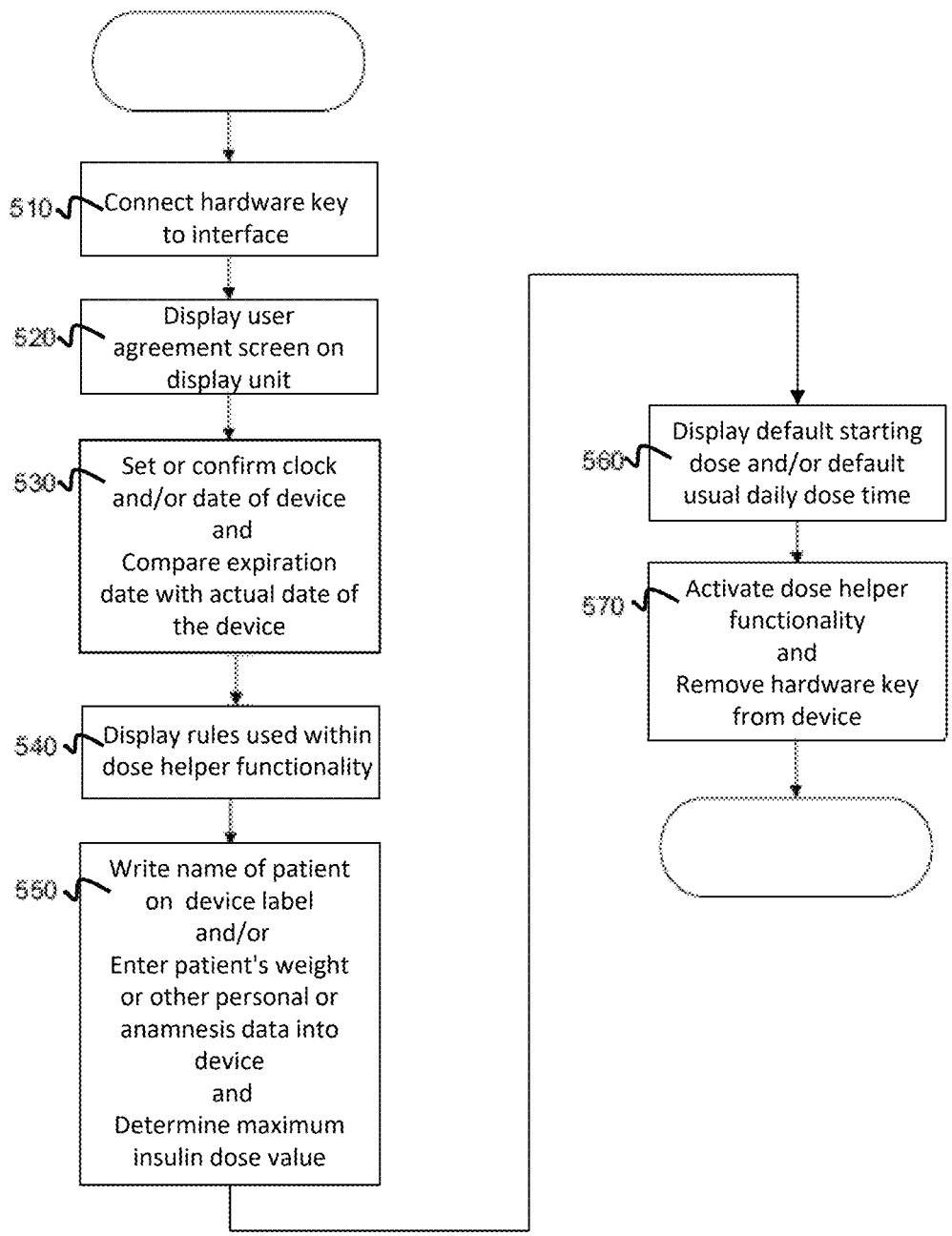
FIG. 5 is a flow diagram illustrating steps of a further operating procedure of the medical device according to a preferred embodiment of the invention.

The initialization process with the one chosen hardware key is now described using the diagram depicted in FIG. 5.

At first a hardware key 1810, e.g. a mini USB stick comprising, e.g. HCP initialization data, is connected by the HCP to the interface 170 in step 510. Alternatively, any other kind of memory stick or memory card may be used.

After connection, the initialization data of the hardware key 1810 are transmitted via transceiver unit 1815 and interface 170 to the initialization unit 1920 and preferably encrypted. Now, the initialization unit 1920 which is connected to storage unit 130 chooses initial data from the initial data matrix comprising a set of at least two different data entries for each parameter based on the initialization data of the hardware key. Therefore, the initialization data of the hardware key contains the position of the initial data entry for each initial parameter set in the initial data matrix. For example, the initialization data point to the first data entry of the first parameter set for the first parameter, to the third data entry of the second parameter set for the second parameter, to the second data entry of the third parameter set for the third parameter and so on. The parameters comprise for example the following:

- lower FBG limit (i.e. the lower limit of the FBG target),
- titration type (e.g. normal and fast), which defines the maximal dose increase per x days and therefore the speed of the titration,
- default starting dose,
- default usual dose time,
- dose decrease on low blood glucose and/or hypo symptoms, which defines the amount of dose decrease in case the patient has recorded a hypo or low blood glucose,
- out of target definitions, which defines when the dose helper shall treat the patient again as out of target once he was in target,
- duration of prescription (i.e. the activation time of the dose helper functionality),
- insulin brand name,
- low blood glucose limit, (this parameter may define a dose decrease), very low blood glucose limit, (this is another parameter that may define a dose decrease, more serious than the low blood glucose limit), definitions for patient in target, which defines when the dose helper shall treat the patient as in target, for example a target blood glucose range, absolute maximum dose (i.e. the upper dose limit which may not be exceeded by the dose setting unit 1930), maximum dose, which defines the maximum insulin dose for the patient depending on his/her weight, deactivation time, e.g. after how many days the dose helper functionality 1s deactivated in case of inactivity or insufficient use).

Now the method proceeds to step 520 to display a user agreement screen on the display unit 160. If the HCP declines the user agreement the initialization process is terminated and the dose helper functionality is not activated. If the HCP agrees to the user agreement preferably by pressing the respective soft key 620 the method proceeds to step 530 in which the clock and/or date of the device may be set or confirmed.

In a preferred embodiment the storage unit 1817 of the of the activation key 1810 contains an expiration date which is for example 2 years after production date of the activation key. The initialization unit 1920 of the device 100 compares in step 530 the expiration date with the actual date of the device. If the device date is close to the expiration date, e.g. within one month to the expiration date, a message may be displayed to the HCP that the key will expire shortly. If the expiration date is exceeded the initialization and activation of the dose helper functionality will be terminated. A plausibility check be used in reactivations of the dose helper functionality when the device was already activated at least once in the past. The plausibility check is based on an independent clock that cannot be changed by the user. At the moment of the $1^{st}$ activation of the dose helper functionality, the independent clock is automatically started. Therefore, the clock counts the time from the first activation until the present time. In the case of reactivation the LTM can compare the date entered by the HCP with its date of production plus the time elapsed since the $1^{st}$ activation.

In the next step 540, FBG rules and/or the hypoglycemia rules used within the dose helper functionality are displayed for the HCP. In an example embodiment, these rules may now be changed by the HCP. Then, in step 550 the HCP may be required to write the name of the patient on a label, for example on the back of the device, and/or enter the patient's weight or other personal or anamnesis data of the patient, preferably by using the navigation keys 630. The entered patient's weight may be used by the initialization unit 1920 to determine a maximum insulin dose value, preferably for long-acting insulin.

The method proceeds to step 560 to display the default starting dose and/or a default usual daily dose time selected by the initialization unit 1920 from the initial matrix. The default starting dose and/or a default usual dose time may be changed by the HCP. In a preferred embodiment a reminder is provided by the device which reminds the user to administer the daily long-acting insulin dose. The reminder may be activated or deactivated by the user.

In the following step 570 the HCP is required to activate the dose helper functionality, for example by pressing a soft key 620, and to remove the hardware key 1810 from the device 100. Now the dose helper functionality is initialized and activated and the user may apply this function for example by pressing the dose helper key 637. Preferably, by removing the hardware key 1810 the device is turned off.

In another embodiment a remote computer is used for initialization and activation of the dose helper functionality, wherein the computer comprises the respective software and is connected to the medical device by wire or wirelessly. After starting the software and confirmation of the warning screen, the HCP or another user chooses an initialization template stored in the computer which best fits the needs of the patient for titration. Then, the template data are transmitted to the device and the initialization unit chooses the initial data from the initial data matrix of the storage unit according to the template which are at least partly shown on the computer screen. Now, the HCP or user has the possibility to change one or more default initial data and after that activates the dose helper functionality using the remote computer.

In a further embodiment the HCP or another user uses an internet application for receiving security data like a security code after entering a question code received from the medical device. The security code is entered into the medical device and allows the user to access the initialization and activation function of the dose helper functionality. Within this function the user may choose one of several templates containing initial data stored in the initial data matrix according to the needs of the patient. After passing a change menu providing the possibility to change default initial data and reviewing at least part of the initial data the user may confirm activation of the dose helper functionality.

In order to run the dose helper functionality correctly and successfully it is preferred that the blood glucose measurement values which are FBG values are identified. Therefore these blood glucose measurement values may be tagged by the user. In order to make the tagging easier for the patient the tagging may be realized by defining a certain predefined time interval (e.g. 5 a.m. to 11 a.m.) which is stored in the storage unit 130 and may be changed by the user in the settings mode. A blood glucose measurement value detected within this time interval receives the pre-tagging "FBG value". The user now only needs to confirm this tag, for example by using the soft keys 620. Now, the measured blood glucose measurement value is stored in the storage unit 130 as a FBG value along with the date and time of the measurement. If the user does not confirm this pre-tagging, no tag is stored along with this value. Preferably, the user may choose other tags such as "pre meal" or "after meal", for example by using the navigation keys 630.

For further explanation and possibilities with regard to the dose helper functionality and the blood glucose measurement the disclosure of WO 2010/89304 A1 is incorporated herein by reference.

In cases where the data set is not sufficient or inadequate to calculate an insulin dose because, for instance, the patient does not take measurements regularly or does not store the administered insulin doses, the dose helper functionality of the device may display the message that no recommendation can be provided until an adequate data set is established. Further, a dose recommendation cannot be given if the patient is in a situation where a preemptive dose change is required based on other factors (e.g. illness, change of other diabetes medication, change in lifestyle, exercise, vacation) and time changes due to travelling of more than a predefined time range, for example more than three hours.

It shall be emphasized that in a preferred embodiment the patient makes the final decision on a dosing. The result of the dose setting unit 1930 may only be a suggestion in this case. The patient may confirm this dose or change it. The inventive device is seen as a support similar to the on-paper treatment algorithms for self-titration that may provide a direction. Still, the patient is taught to observe other rules for taking into account other factors like health, activity etc. in order to safely manage the insulin dosing, which may lead to the patient overruling the dose suggestion or calling their HCP if they are unsure.

In an example embodiment, device 100 is realized as a two-part device, wherein storage unit 130, the receiving unit 120, the determining unit 140, the user input unit 150, the display unit 160, the interface unit 170, the dose setting unit 1930 and the initiation unit 1920 are realized as a software program (application or "app") to run on the hardware of a smartphone. The storage unit 130 may additional store the HCP's phone number and offers the user to call the HCP for advice if needed. The call could be initiated by just one button click, offered by the app, for example by selection a respective field on the display. The keys 620, 630, 635 and 637 are realized in this case as button fields on the display of a touchscreen.

What is claimed is:

1. A medical device for supporting health control, the medical device comprising:
   a receiver unit capable of receiving information regarding a current location and/or a current time zone of the medical device;
   a user interface;
   a storage unit storing instructions, the storage unit including a semiconductor memory, a hard disk memory or an on-chip memory;
   one or more processors configured to execute the instructions to cause the medical device to implement a dose helper functionality by performing operations comprising:
      receiving information regarding a current location and/or a current time zone of the medical device via the receiver unit;
      where information is received regarding the current location of the medical device and information is not received regarding the current time zone of the medical device, determining the current time zone of the medical device based on the current location information;
      determining whether a time difference between the current time zone of the medical device and a time zone of the medical device at a last known dose is more than a predefined maximum time change value;
      where the time difference is not more than the predefined maximum time change value:
         executing the dose helper functionality including employing a titration method to determine a basal long-acting insulin dose value or a corrective amount of basal long-acting insulin to be administered by a patient to the patient based, at least in part, on a measured physiological parameter, wherein the titration method starts at a starting dose of the basal long-acting insulin and the dose helper functionality guides the patient by modifying a dose of the basal long-acting insulin step by step over time to a final dose of the basal long-acting insulin that keeps the patient in a predefined target glucose level by determining the basal long-acting insulin dose value or the corrective amount of basal long-acting insulin to be administered by the patient at each step; and
      where the time difference is more than the predefined maximum time change value:
         preventing the dose helper functionality from determining the basal long- acting insulin dose value or the corrective amount of basal long-acting insulin.

2. The medical device according to claim 1, wherein the measured physiological parameter is a blood glucose value.

3. The medical device according to claim 1, wherein the user interface includes a display unit; and
   wherein the operations further comprise, where the time difference is more than the predefined maximum time change value:
      providing a warning to the patient by providing a warning display using the display unit; and/or
      providing a display informing the patient that no dose suggestion or dose increase was determined using the display unit.

4. The medical device according to claim 1, wherein the operations further comprise:
   checking whether a current time is within a predefined time interval from a time of administration of a last known dose or whether the time of administration of the known dose is separated from the current time by less than the predefined time interval; or
   checking whether the current time is within a usual dose time where the usual dose time is a predefined time range of day.

5. The medical device according to claim 1, wherein the determined basal long-acting insulin dose value or the corrective amount of basal long-acting insulin to be administered is further based, at least in part, on at least one of: exercise information, nutrition facts, additional fast-acting insulin doses, hypoglycemia symptoms, a hyperglycemic event, and/or stress information.

6. The medical device according to claim 1, wherein:
   the receiver unit comprises: a Global System for Mobile Communications (GSM) receiver, a Global Positioning System (GPS) receiver, a GPS module, a radio broadcast receiver capable of interpreting a Radio Data System (RDS) signal, a radio clock receiver in order to determine the local time, or any combination of the aforementioned.

7. The medical device according to claim 1, wherein the medical device has an expiry date; and
   wherein the operations further comprise:
      preventing use of the dose helper functionality where a current date is past the expiry date; or
      preventing use of the dose helper functionality where the current date is past the expiry date and the dose helper functionality has not been reactivated.

8. The medical device according to claim 1, wherein the medical device further comprises a blood glucose measurement unit.

9. The medical device according to claim 8, wherein the dose helper functionality can be initialized and activated, and deactivated without influencing an operation of the blood glucose measurement unit.

10. The medical device according to claim 1,
   wherein the storage unit includes a first memory configured to store an initial data matrix with at least one initial parameter set containing at least two initial data entries for one parameter of a dose helper functionality;
   wherein the medical device further comprises a second receiver unit configured to receive initialization data; and
   wherein the operations further comprise:
      selecting, based at least in part on the initialization data, one data entry for each initial parameter set as initial data or one initial parameter template containing a reference to one data entry for each initial parameter set as initial data; and activating execution of the dose helper functionality based on the selected initial data.

11. The medical device of claim 10, wherein the second receiver unit is configured to receive security data; and wherein the activation of the execution of the dose helper functionality is further based, at least in part, on the received security data.

12. The medical device of claim 11, wherein the second receiver unit is configured to receive the initialization data and security data from a memory or second storage unit separate from and different than the first memory and the storage unit.

13. The medical device according to claim 11, wherein the operations further comprise:

modifying at least one of the selected initial data entries, and permitting or restricting modification of at least one of the selected initial data entries based, at least in part, on the security data.

14. The medical device according to claim 1, wherein the medical device is configured to facilitate contact between the patient and a pre-defined health care professional for the patient when the patient is locked out from the dose helper functionality.

15. The medical device according to claim 14, wherein the medical device is configured to contact the pre-defined health care professional via a call or a message.

16. The medical device according to claim 1, wherein the predefined maximum time change value is three hours.

17. A non-transitory storage medium storing instructions that when executed by one or more processors of a medical device that includes a receiver unit capable of receiving a current location and/or a current time zone of the medical device, cause the medical device to perform operations comprising:

receiving information regarding a current location and/or a current time zone of the medical device;

where information is received regarding the current location of the medical device and information is not received regarding the current time zone of the medical device, determining the current time zone of the medical device based on the current location information;

determining whether a time difference between the current time zone of the medical device and a time zone of the medical device at a last known dose is more than a predefined maximum time change value;

where the time difference is not more than the predefined maximum time change value:

executing the dose helper functionality including employing a titration method to determine a basal long-acting insulin dose value or a corrective amount of basal long-acting insulin to be administered by a patient to the patient based, at least in part, on a measured physiological parameter, wherein the titration method starts at a starting dose of the basal long-acting insulin and the dose helper functionality guides the patient by modifying a dose of the basal long-acting insulin step by step over time to a final dose of the basal long-acting insulin that keeps the patient in a pre-defined target glucose level by determining the basal long-acting insulin dose value or the corrective amount of basal long-acting insulin to be administered by the patient to the patient at each step and providing a recommendation based on the determination of the basal long-acting insulin dose value or the corrective amount of basal long-acting insulin to the patient via a user interface of the medical device; and where the time difference is more than the predefined maximum time change value:

preventing the dose helper functionality from recommending the basal long-acting insulin dose value or the corrective amount of basal long-acting insulin.

18. The non-transitory storage medium according to claim 17, wherein the medical device further comprises a display unit; and wherein the operations further comprise, where the time difference is more than the predefined maximum time change value:

providing a warning to the patient by providing a warning display; and/or providing a display informing the patient using the display unit that no dose suggestion or dose increase was determined.

19. The non-transitory storage medium according to claim 17, wherein the operations further comprise:

where the time difference is more than the predefined maximum time change value:

the dose helper functionality is prevented from recommending the basal long-acting insulin dose value or the corrective amount of basal long-acting insulin by locking the patient out from the dose helper functionality, and facilitating contact between the patient and a pre-defined health care professional for the patient when the patient is locked out from the dose helper functionality.

20. The non-transitory storage medium according to claim 19, wherein facilitating contact between the patient and the pre-defined health care professional for the patient when the patient is locked out from the dose helper functionality comprises:

presenting a selectable option on a user interface of the medical device to contact the pre-defined health care professional via a call or a message; and contacting the pre-defined health care profession via the call or the message based on receipt of a selection by the user of the selectable option.

21. The non-transitory storage medium according to claim 17, wherein the predefined maximum time change value is three hours.

* * * * *